(12) United States Patent
Sandu et al.

(10) Patent No.: US 7,845,235 B2
(45) Date of Patent: Dec. 7, 2010

(54) NON-INVASIVE SYSTEM AND METHOD FOR MEASURING VACUUM PRESSURE IN A FLUID

(76) Inventors: Costin Sandu, 26356 Vintage Woods Rd. Apt. 3C, Lake Forest, CA (US) 92630; Tate Parham, 33 korite, Rancho Santa Margarita, CA (US) 92688

(*) Notice: Subject to any disclaimer, the term of this patent is extended or adjusted under 35 U.S.C. 154(b) by 83 days.

(21) Appl. No.: 12/291,142

(22) Filed: Nov. 6, 2008

(65) Prior Publication Data

US 2009/0114027 A1    May 7, 2009

Related U.S. Application Data

(60) Provisional application No. 61/002,038, filed on Nov. 6, 2007.

(51) Int. Cl.
*G01L 13/02* (2006.01)
(52) U.S. Cl. ...................................................... 73/715
(58) Field of Classification Search .................. None
See application file for complete search history.

(56) References Cited

U.S. PATENT DOCUMENTS

| | | | |
|---|---|---|---|
| 4,120,206 A * | 10/1978 | Rud, Jr. | ...... 73/718 |
| 4,227,420 A | 10/1980 | Lamadrid | |
| 4,535,635 A | 8/1985 | Claren et al. | |
| 4,555,952 A * | 12/1985 | Jenkins | ...... 73/861.47 |
| 4,972,705 A | 11/1990 | Fryer et al. | |
| 5,337,601 A | 8/1994 | Becker et al. | |
| 5,392,653 A | 2/1995 | Zanger et al. | |
| 5,400,646 A | 3/1995 | Kraus et al. | |
| 5,557,972 A | 9/1996 | Jacobs et al. | |
| 5,661,245 A | 8/1997 | Svoboda et al. | |
| 5,753,820 A | 5/1998 | Reed et al. | |
| 5,983,727 A | 11/1999 | Wellman et al. | |
| 6,058,779 A | 5/2000 | Cole | |
| 6,941,813 B2 | 9/2005 | Boukhny et al. | |
| 6,955,073 B2 | 10/2005 | Morgan et al. | |
| 7,178,402 B2 | 2/2007 | Wanka et al. | |
| 2006/0027028 A1 * | 2/2006 | Ariav et al. | ...... 73/820 |

FOREIGN PATENT DOCUMENTS

| | | |
|---|---|---|
| WO | WO/2008/067681 | 6/2008 |
| WO | WO/2008/072527 | 6/2008 |
| WO | WO/2008/101374 | 8/2008 |
| WO | WO/2008/128829 | 10/2008 |

* cited by examiner

*Primary Examiner*—Andre J Allen
(74) *Attorney, Agent, or Firm*—Matt Mushet

(57) ABSTRACT

A noninvasive system and method for measuring vacuum pressure in a fluid in accordance with the present invention generally includes a chamber with two interconnected diaphragms having different surface areas and a force transducer that makes contact with the smaller area diaphragm. When a pressure level less than atmospheric occurs inside the chamber, the smaller area diaphragm presses with a force on the force sensor. As the pressure level in the chamber decreases, the force on the sensor increases. The present system is intended for, but not limited to, use in a Phacoemulsification machine, where it will serve to measure the vacuum in a fluid without contaminating the fluid with previous uses of the system or with any components of the system which are unable to undergo a sterilization process.

20 Claims, 6 Drawing Sheets

NON-INVASIVE SYSTEM AND METHOD FOR MEASURING VACUUM PRESSURE IN A FLUID

CROSS REFERENCE TO RELATED APPLICATIONS

This application claims the benefit of 35 U.S.C. §119 and the filing date of provisional application 61/002,038, filed Nov. 6, 2007.

FIELD OF INVENTION

The present invention relates to the field of pressure measuring systems. More specifically, the invention relates to systems that non-invasively measure the degree of vacuum in a fluid.

BACKGROUND OF THE INVENTION

In essence, a vacuum is a volume of space that is void of any matter such that the gaseous pressure of this volume of space is less than standard atmospheric pressure. Simply measuring the vacuum in a fluid is neither new nor novel, and the methods to do so do not need to be mentioned in this application, except to say that these prior methods, when applied to a living system, have generally been invasive in nature and therefore at times were susceptible to cross contamination of the fluids in which the vacuum is being measured. Thus, there exists a need in the art, especially in the area of ophthalmic instruments such as Phacoemulsification machines, for a more hygienic and noninvasive system to measure fluid in a vacuum.

Phacoemulsification machines are used for removing cataracts, or crystalline manifestations, from the eye. The machine may include a probing device, which typically constitutes an ultrasound driven hollow needle. In such a case, the needle is inserted into the eye through a small incision in the opaque layer of tissue surrounding the pupil, and vibrates at ultrasonic frequency to emulsify any crystalline manifestations that may be present. The emulsified particles of cataract are then aspirated through an opening at the tip of the hollow needle. The aspiration process is, in a sense, two interconnected operations. The first operation of the process is the actual removal of the cataract fragmentations through the application of a vacuum pressure. During the removal of the fragmentations, there must be a continuous circulation of fluid through the eye. This is provided by the second operation, in which the hollow needle supplies this circulation of fluid.

The entire process is a delicate one, as the pressure in the eye must be constantly measured and maintained to prevent a number of problems. For example, during the removal operation, any blockage in the hollow needle, possibly created during the passage of one cataract fragmentation, may cause a void, or vacuum, to build in said needle. In such an instance, it may be necessary to apply a higher level of pressure in order to dislodge the blockage. Failure to adequately measure and control the fluid pressure during this process may result in the sudden ejection of the blockage followed by a rapid influx of fluid from the eye into the void. If this fluid is not replaced with sufficient speed, it could lead to the subsequent collapse of the eye chamber. Another way to remove a blockage from the hollow needle is to reverse the flow of fluid in the needle to expel the blocking fragmentation. Again, however, if the fluid pressure is not adequately measured and controlled, the ramifications could be extremely problematic. In this situation, the vacuum pressure would be negative, so when the blockage is removed there may be a subsequent flooding of the eye chamber leading to an inflation of the eye. Furthermore, as discussed above, the use of a standard pressure measuring system to monitor these pressures is not an adequate solution to the problem, as cross contamination of fluids will then become an issue.

The industry has devised a number of different systems in trying to fulfill this need for a non-invasive system of measuring vacuum in a fluid, both respective and irrespective of use with Phacoemulsification machines. However, all of these solutions have been shown to suffer from deficiencies when utilized in this application. One such system involves separating the measured fluid from another fluid, usually air or gel, with a membrane, and measuring the pressure in the other fluid. Another such system involves using an elastic element to load a force transducer, for example, pressing a tube that contained the measured fluid to a force sensor and measuring the fluid pulling force on that element using the differences between the zero atmospheric level and the vacuum level. The two aforementioned systems, though operable, suffer from increased levels of hysteresis (path dependence) and volume variance. A third method uses a diaphragm exposed on one side to the fluid and on the other side to a force transducer. The pulling force on the diaphragm is measured usually using a magnetic coupling between the diaphragm and the force sensor. However, this third system can suffer from being overly robust in construction. Thus, there still exists a need in the art for a simply constructed, noninvasive system for the measuring of vacuum pressure in a fluid that will not suffer from high levels of hysteresis or volume variance.

SUMMARY OF THE INVENTION

A noninvasive system for measuring vacuum pressure in a fluid in accordance with the present invention generally includes a chamber with two interconnected diaphragms, having different surface areas, and a force transducer that makes contact with the smaller area diaphragm. The two different surface areas allow for a pressure differential. When a pressure level less than atmospheric occurs inside the chamber, the smaller area diaphragm presses with a force on the force sensor. As the pressure level in the chamber decreases, the force on the sensor increases. The present system is intended for, but not limited to, use in a Phacoemulsification machine, where it will serve to measure the vacuum in a fluid without contaminating the fluid with previous uses of the system or with any components of the system which are unable to undergo a sterilization process.

In order to differentiate from limitations found in the prior art and to maximize the scope of the invention presently disclosed, it is one object to provide for a system that noninvasively measures vacuum pressure in a fluid. It is considered noninvasive because this system created by the body, tubing and sensor chamber never contact external instrumentation or measuring devices. This presently disclosed system is conducive to ensuring the prevention of cross contamination of fluids from previous or subsequent use. It is another object of the present invention to avoid a system that suffers from hysteresis or volume variance. A third object of the present disclosure is to provide a system that is simply constructed and a method that is easy to follow.

DETAILED DESCRIPTION OF THE PREFERRED EMBODIMENT

In the following description of the various embodiments, reference is made to the accompanying drawings, which form a part hereof, and in which is shown by way of illustration, various embodiments in which the invention may be practiced. It is to be understood that other embodiments may still be utilized and structural and functional modifications may be made without departing from the scope and spirit of the present invention.

Figure 1:
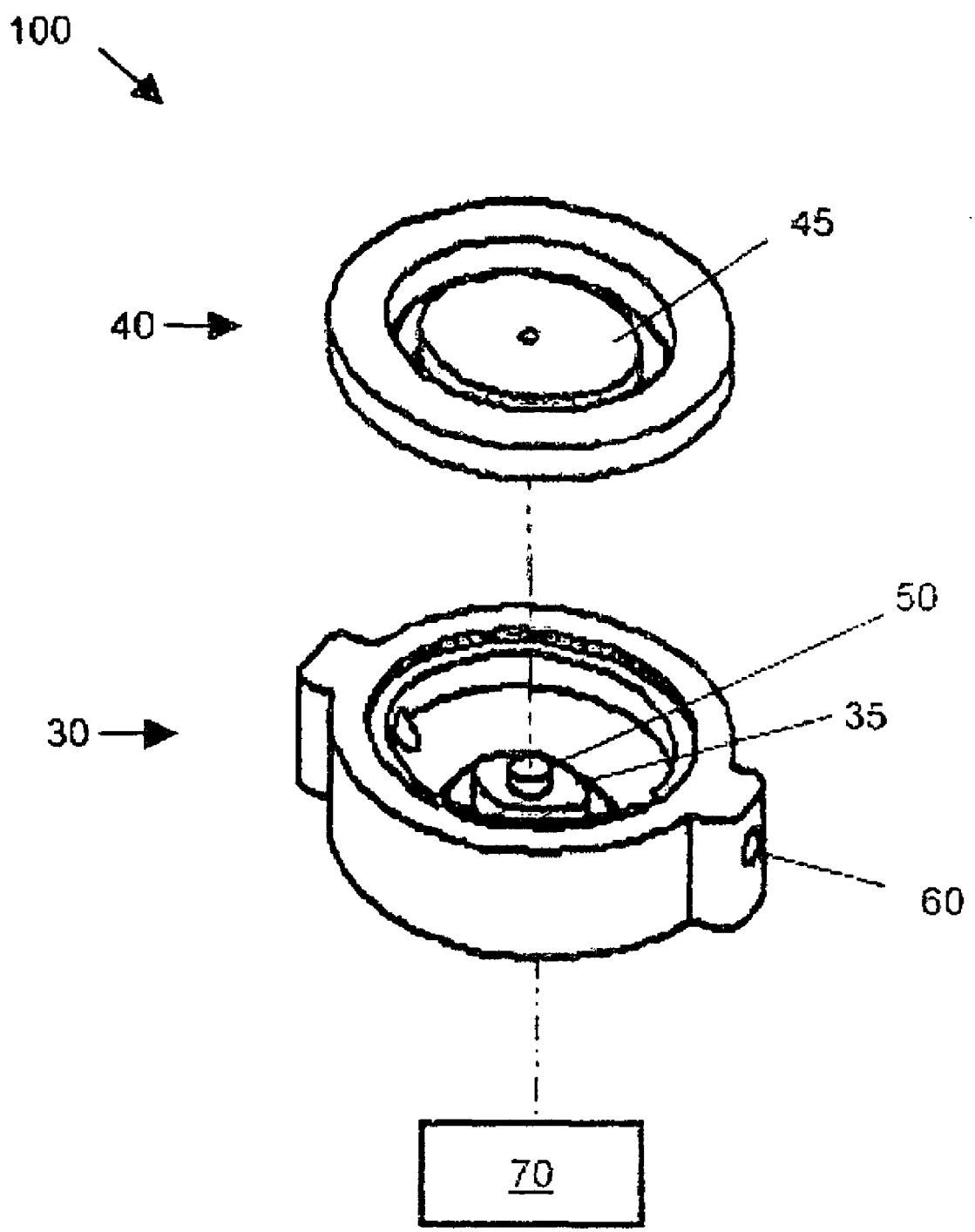
FIG. 1 illustrates an exploded view of a pressure sensor in a noninvasive system for measuring vacuum pressure in a fluid in the preferred embodiment of the present invention.

Referring to FIG. 1, an exploded view of a pressure sensor of the preferred embodiment of a system for noninvasively measuring the vacuum pressure in a fluid is shown. Pressure sensor chamber 100 is shown comprised of lower piece 30 and upper piece 40. Lower piece 30 comprises small diaphragm 35 while upper piece 40 comprises large diaphragm 45, whereby small diaphragm 35 and large diaphragm 45 are interconnected by diaphragm bridge 50. In the preferred embodiment, the entire pressure sensor is less than one inch in diameter and may be ovular or circular from the top down. In this embodiment, chamber 100 is constructed of biocompatible and autoclavable silicon but it can be envisioned to be constructed either wholly or partially of plastic, rubber, glass or any other suitable material known to one of ordinary skill in the art. Force transducer 70, which is preferred to be an industry standard force transducer, is held by a support and directly contacts small diaphragm 35. Fluid inlet 60 and fluid outlet 65 (not shown) bookend chamber 100 and are openly connected within chamber 100 in such a way so that fluid inlet 60, fluid outlet 65 and chamber 100 may form one continuous channel which circumscribe diaphragm bridge 50. It should be clear to one of ordinary skill in the art that the function of fluid inlet 60 and outlet 65 are to serve as entry and exit paths for any fluid that is desired to pass through chamber 100 while the presently disclosed system for measuring vacuum pressure of a fluid is in use.

During operation, a fluid will flow from fluid inlet 60 through chamber 100 and exit out of fluid outlet 65. During this flow of fluid, small diaphragm 35 and large diaphragm 45, which are preferably glued together at diaphragm bridge 50, will react to variances in pressure of this fluid. When a pressure level less than atmospheric, or simply less than the pressure of the surroundings, occurs inside chamber 100 and creates a vacuum, small diaphragm 35 will exert a force on force transducer 70. As the pressure in chamber 100 decreases relative to the surroundings, the force on transducer 70 increases proportionally. Therefore, the disclosed system will immediately be able to detect changes in the pressure of any fluid within chamber 100, while eliminating the risk of cross contamination from prior uses by keeping many of the requisite elements external. This allows for minimal sterilization to be necessary between uses. It should also be apparent to one of ordinary skill in the art that the ability of fluid to freely flow through chamber 100 will reduce problems that may be caused by hysteresis or volume variance.

Figure 2A:
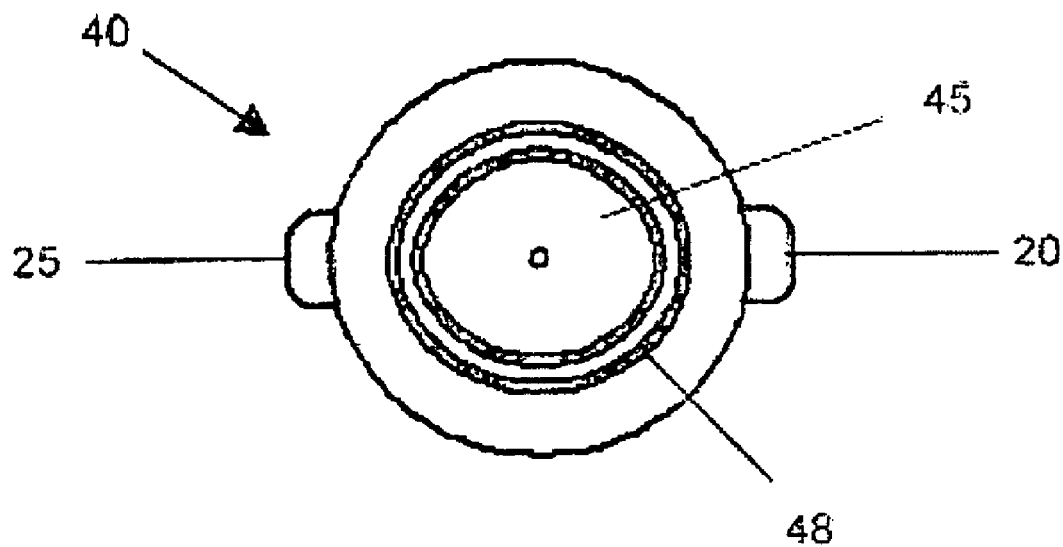
FIG. 2a illustrates a top view of a pressure sensor chamber in the preferred embodiment of the present invention.

Now referring to FIG. 2a, a top view of the entire pressure sensor chamber of the preferred embodiment of a system for noninvasively measuring the vacuum pressure in a fluid is shown. Inlet wing 20 and outlet wing 25 on lower piece 30 can be viewed extending out beyond upper piece 40. Large diaphragm 45 can best be viewed from this angle, having a preferable surface area of approximately three times smaller diaphragm 35 (not shown). Although, any difference in surface areas will allow the presently disclosed sensor to function. Ribbed crease 48 can also be seen surrounding large diaphragm 45 which allows for movement while in use. The normal stiffness of ribbed crease 48 is very slight and can be tared when computing measurements. Also, the position of ribbed crease 48 is indented slightly below the surface plane of upper large diaphragm 45 and upper piece 40. This positioning allows upper piece 40 and lower piece 30 to fit snugly together.

Figure 2B:
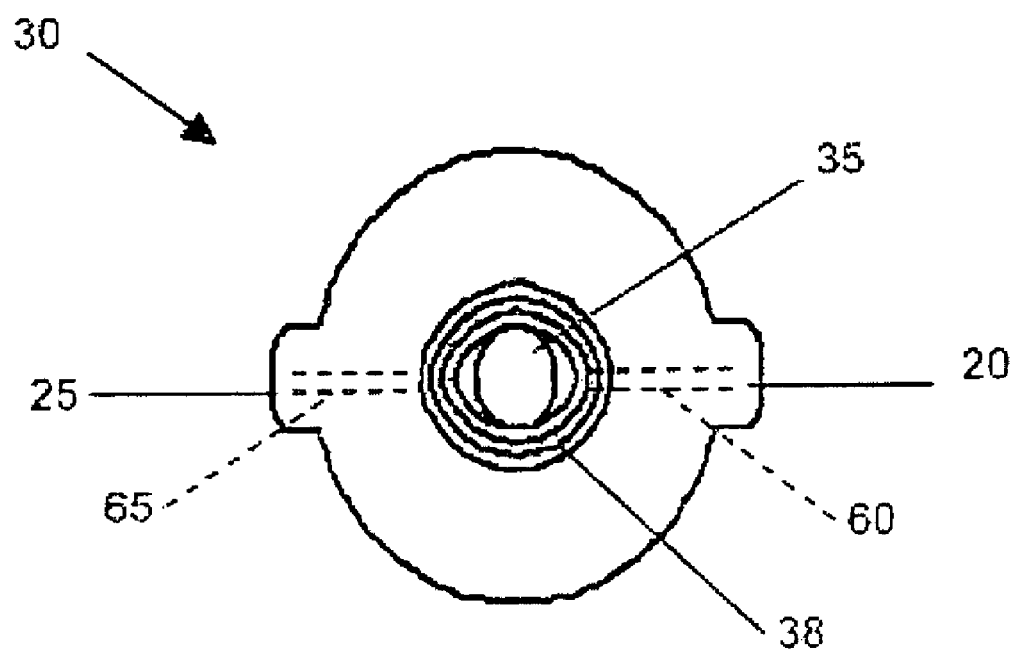
FIG. 2b illustrates a bottom view of a pressure sensor chamber in the preferred embodiment of the present invention.

Now referring to FIG. 2b, a bottom view of the entire pressure sensor chamber of the preferred embodiment of a system for noninvasively measuring the vacuum pressure in a fluid is shown. Again, inlet wing 20 and outlet wing 25 on lower piece 30, which house fluid inlet 60 and fluid outlet 65 respectively, can be viewed extending outward. Small diaphragm 35 can best be viewed from this angle. Depending on its size, small diaphragm 35 may or may not expand in a radial stepping manner before reaching ribbed crease 38 for support purposes. Ribbed crease 38 is preferably smaller in diameter than ribbed crease 48, in FIG. 2a, but it provides the same minimal rigidity. Ribbed crease 38 similarly extends into chamber 100 and below the plane of lower piece 30.

Figure 3A:
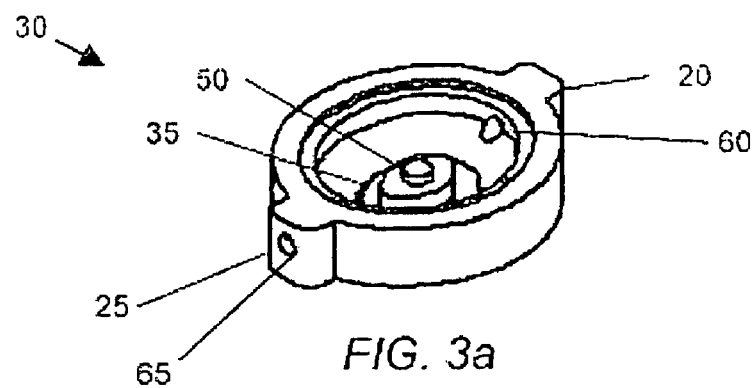
FIG. 3a illustrates a top angled view of the lower piece comprising a diaphragm of smaller surface area in the preferred embodiment of the present invention.

Now referring to FIG. 3a, a top angled view of the lower piece comprising a diaphragm of smaller surface area in the preferred embodiment of the present invention is shown. Lower piece 30 can be seen in more detail from this inward view which comprises inlet wing 20, fluid inlet 60, outlet wing 25, fluid outlet 65, small diaphragm 35 and diaphragm bridge 50. It can easily be seen that the fluid path crosses only through lower piece 30, but it could be envisioned to conduct fluid through chamber 100 in any fashion that creates this continuously sealed cavern.

Figure 3B:
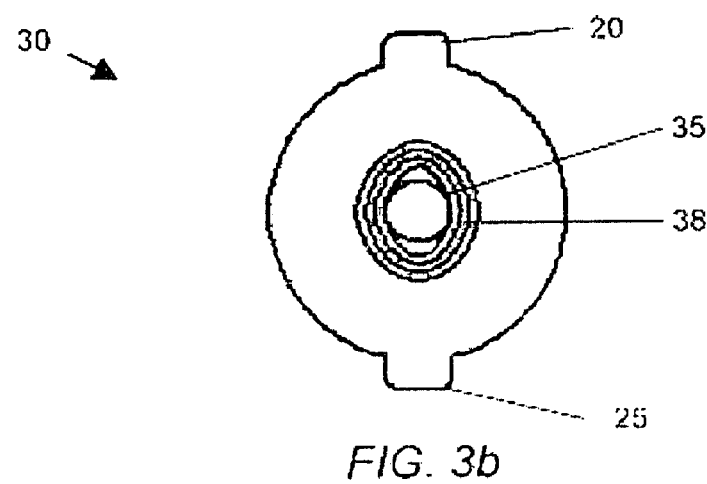
FIG. 3b illustrates a bottom view of the lower piece comprising a diaphragm of smaller surface area in the preferred embodiment of the present invention.
Figure 3C:
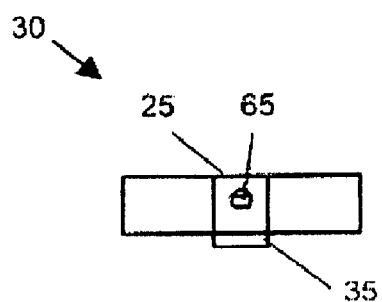
FIG. 3c illustrates a front view of the lower piece comprising a diaphragm of smaller surface area in the preferred embodiment of the present invention.
Figure 3D:
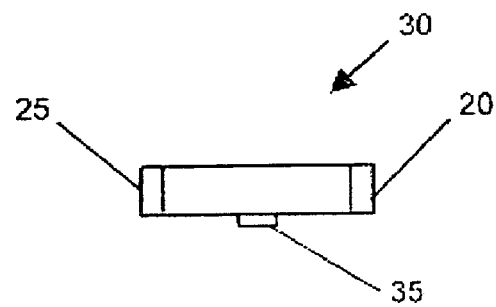
FIG. 3d illustrates a side profile view of the lower piece comprising a diaphragm of smaller surface area in the preferred embodiment of the present invention.

Now referring to FIG. 3b, a bottom view of the lower piece comprising a diaphragm of smaller surface area in the preferred embodiment of the present invention is shown. Besides inlet and outlet wings 20, 25, this view showcases ribbed crease 38, described infra. It should be pointed out that in the preferred embodiment of the present disclosure, small diaphragm 35 actually extends beyond the plane of lower piece 30, which can more easily be seen in the front and side profile views of FIGS. 3c and 3d. In FIG. 3c, fluid outlet 65 is turned to face out, while in FIG. 3d, outlet wing 25 can be seen facing left. An important significance to FIGS. 3a-d is that lower piece 30 is thicker than upper piece 40, so as to offer a cup-like shape in this embodiment.

Figure 4A:
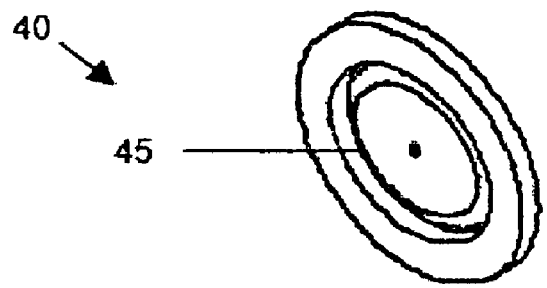
FIG. 4a illustrates a top angled view of the upper piece comprising a diaphragm of larger surface area in the preferred embodiment of the present invention.

Now referring to FIG. 4a, a top angled view of the upper piece comprising a diaphragm of larger surface area in the preferred embodiment of the present disclosure is shown. As previously described, upper piece 40 comprises large diaphragm 45.

Figure 4B:
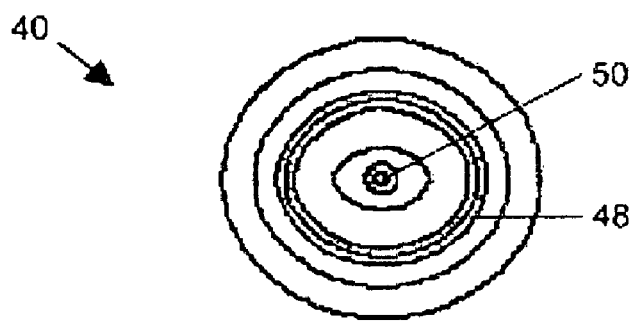
FIG. 4b illustrates a bottom view of the upper piece comprising a diaphragm of larger surface area in the preferred embodiment of the present invention.

Now referring to FIG. 4b, a bottom view of the upper piece comprising a diaphragm of larger surface area in the preferred embodiment of the present disclosure is shown. In this embodiment, larger diaphragm 45 converges on the underside to form cone shaped diaphragm bridge 50. Although bridge 50 can be found on both upper piece 40 and lower piece 30, it combines to form one structure when the pieces are assembled together by methods known in the art.

Figure 4C:
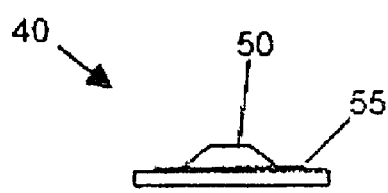
FIG. 4c illustrates a front view of the upper piece comprising a diaphragm of larger surface area in the preferred embodiment of the present invention.
Figure 4D:
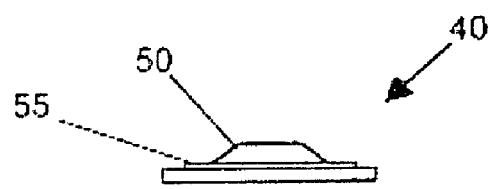
FIG. 4d illustrates a side profile view of the upper piece comprising a diaphragm of larger surface area in the preferred embodiment of the present invention.

Now referring to FIGS. 4c and 4d, a front view and side profile view of the upper piece comprising a diaphragm of larger surface area in the preferred embodiment of the present disclosure is shown. The conical shape of the upper portion of bridge 50 can easily be seen from this angle. Also locking rung 55, which aids in making a snug connection is shown elevated above upper piece 40.

Figure 5:
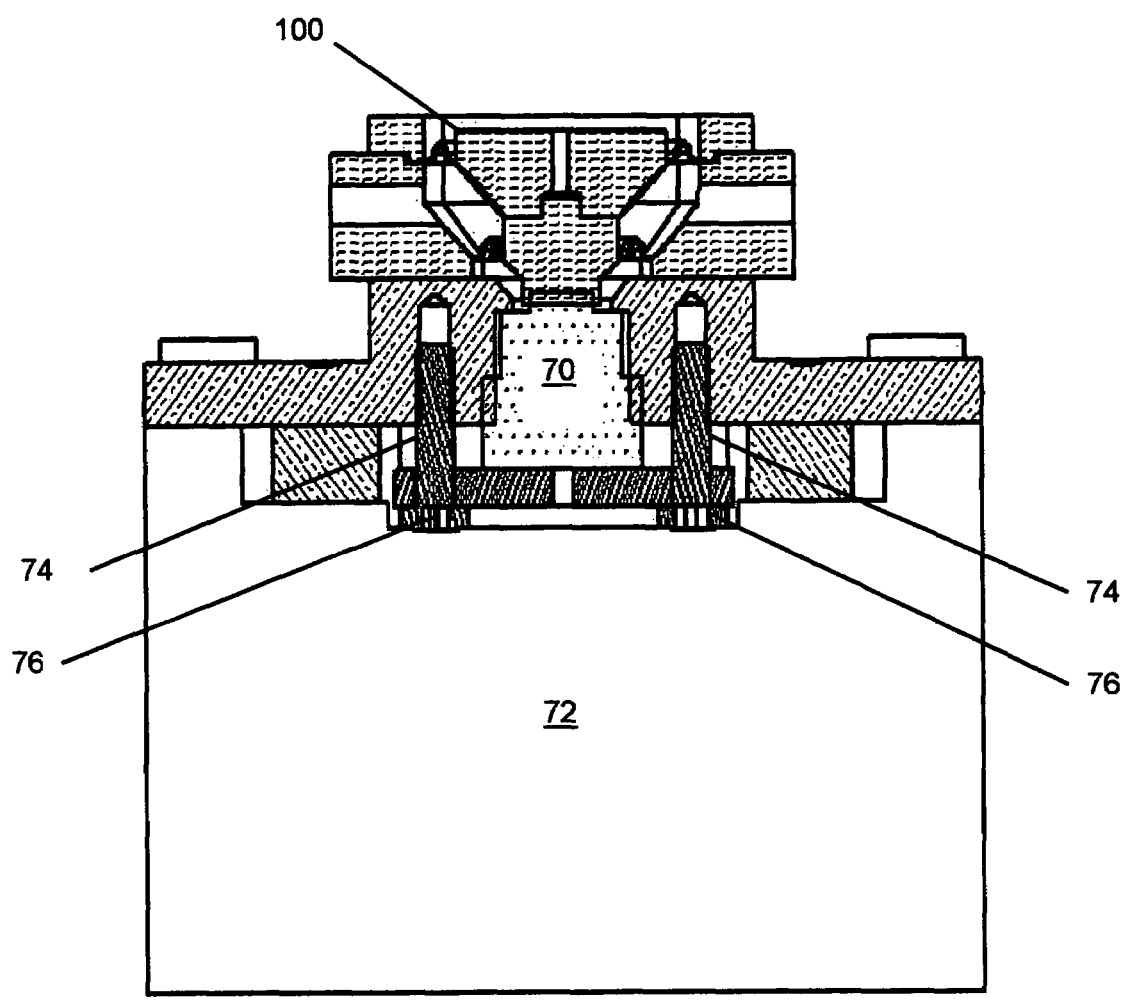
FIG. 5 shows a cross section of the pressure sensor chamber comprising its upper and lower pieces secured into a base plate with a transducer in the preferred embodiment of the present invention.

Now referring to FIG. 5, a cross section of the chamber comprising its upper and lower pieces is shown. Chamber 100 can be seen resting atop force transducer 70. Force transducer 70 in turn sits on base plate 72 and is secured by clamps 74 using clamp screws 76. This view best shows how the system presently described can be used in conjunction with many types of medical and surgical devices, including but not limited to Phaco-emulsification machines.

Figure 6:
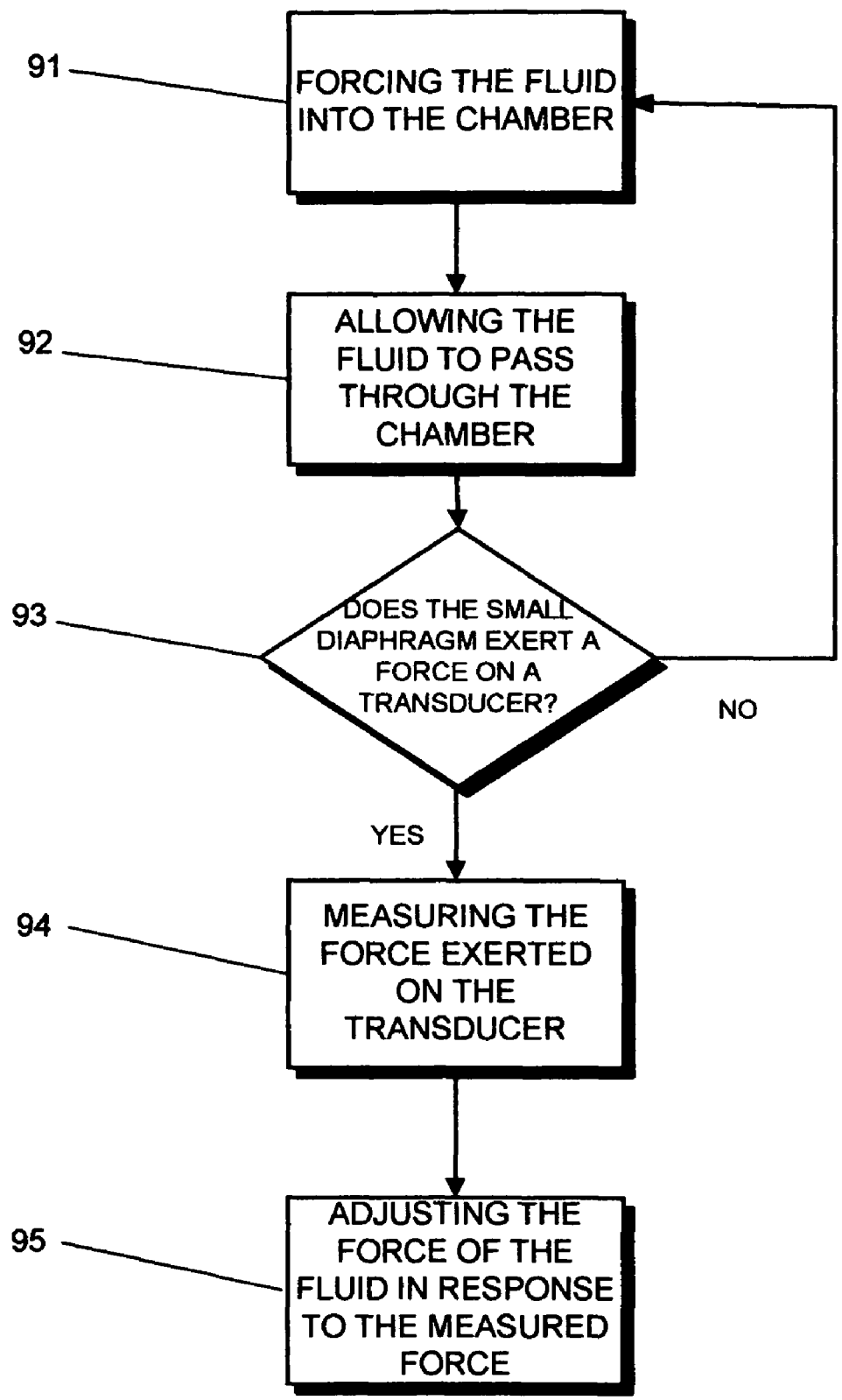
FIG. 6 shows a flowchart of a method of using the pressure sensor chamber in a noninvasive system for measuring vacuum pressure in a fluid in the preferred embodiment of the present invention.

Now referring to FIG. 6, a flowchart of one method of using the pressure sensor chamber in a noninvasive system for measuring vacuum pressure in a fluid in the preferred embodiment of the present disclosure is shown. In step 91, a Phacoemulsification machine connected by tubing to the system presently described is used to dissolve a cataract from an eye. In step 92, any fluid, such as saline solution is used to wash and maintain pressure in the eye. The fluid is then sucked to the presently disclosed system through fluid inlet 60. In step 92, the vacuum pressure of the fluid is measured from a transducer in contact with smaller diaphragm 35. In step 94, the system continuously allows fluid to flow through chamber 100 and back to the eye through fluid outlet 65. In step 95, the system compensates for affected pressure readings by increasing suction force and/or instantaneously reversing suction force until the blockage is cleared. If the pressure reading remains unaffected, no change occurs. After step 95, the system continues to measure and maintain the pressure of fluid in the eye until the operation procedure is accomplished.

The present invention includes any novel feature or combination of features disclosed herein either explicitly or any generalization thereof. While the invention has been described with respect to specific examples including presently preferred modes of carrying out the invention, those skilled in the art will appreciate that there are numerous variations and permutations of the above described apparatus. Thus, the spirit and scope of the invention should be construed broadly as set forth in the previous specification or appended claims.

What is claimed is:

1. A noninvasive system for measuring vacuum pressure in a fluid, comprising:
    a first diaphragm;
    a second diaphragm interconnected with said first diaphragm by a bridge such that the interconnection of said first diaphragm and said second diaphragm form a chamber for the passage of said fluid through said chamber, wherein the surface area of said second diaphragm is less than said first diaphragm; and
    a force transducer directly coupled to said second diaphragm such that if pressure inside said chamber decreases below external pressure, said smaller second diaphragm will apply a measurable proportionate force on said transducer.

2. The system of claim 1, further comprising at least one fluid passageway, said at least one passageway providing for the inlet or outlet of said fluid from said chamber.

3. The system of claim 2, wherein said at least one fluid passageway have different diameters.

4. The system of claim 2, wherein said at least one fluid passageway are located from 5 degrees to 90 degrees from each other in any direction around the diameter of said chamber.

5. The system of claim 1, further comprising a diaphragm bridge that connects the cores of said first diaphragm and said second diaphragm.

6. The system of claim 5, wherein said diaphragm bridge is generally conical in shape, with the base of said bridge directly contacting said first diaphragm.

7. The system of claim 5, wherein said diaphragm bridge and an inner side of said chamber is lined, coated, graphed, mixed, blended or striped with a material different than the rest of said chamber.

8. The system of claim 1, further comprising at least one ribbed area around said first diaphragm and said second diaphragm.

9. The system of claim 8, wherein said ribbed area has a thickness from 0.1 millimeter to 1.5 millimeters.

10. The system of claim 1, wherein said first diaphragm, said second diaphragm, and said chamber are composed of a biocompatible material.

11. The system of claim 1, wherein said first diaphragm, said second diaphragm, and said chamber are composed of a material that can be heated up to 450 degrees Fahrenheit without losing any of the basic properties of said material.

12. The system of claim 1, wherein said system forms a portion of a Phacoemulsification machine or Phaco-handpiece.

13. The system of claim 1, wherein said chamber has a capacity from 0.75 cubic centimeters to 5 cubic centimeters.

14. A method of using the system of claim 1 to measure a vacuum pressure of a fluid comprising the steps of:
    forcing said fluid into a chamber, said chamber formed by the connection or assembly of a large diaphragm and a small diaphragm, and said chamber comprising at least one fluid passageway;
    allowing said fluid to pass through said chamber;
    detecting whether said small diaphragm exerts a positive or negative force on a transducer;

measuring the force exerted on said transducer;

allowing said fluid to exit said chamber; and adjusting the force of said fluid in response to an increase or a decrease in said measured force on said transducer.

15. The method of claim 14, further comprising the step of repeating said method until said measured force is approximately zero.

16. The method of claim 15, wherein said step of measuring said force is accomplished with the assistance of computer software provided by a Phacoemulsification machine.

17. The method of claim 15, wherein said method is used in an operation to remove at least one piece of cataract from the tissues of an eye.

18. The method of claim 15, wherein said vacuum pressure is between 760 Torr. and $1 \times 10^{-5}$ Torr.

19. The method of claim 15, wherein said fluid enters said chamber passively.

20. The method of claim 15, wherein said fluid is forced to exit said chamber.

* * * * *